(12) United States Patent
Jan et al.

(10) Patent No.: US 8,747,807 B2
(45) Date of Patent: Jun. 10, 2014

(54) UZM-5, UZM-5P, AND UZM-6 CRYSTALLINE ALUMINOSILICATE ZEOLITES AND METHODS FOR PREPARING THE SAME

(75) Inventors: Deng-Yang Jan, Elk Grove Village, IL (US); Jaime G. Moscoso, Mount Prospect, IL (US); Raelynn M. Miller, LaGrange, IL (US); Susan C. Koster, Carpentersville, IL (US); Julio C. Marte, Carol Stream, IL (US)

(73) Assignee: UOP LLC, Des Plaines, IL (US)

( * ) Notice: Subject to any disclaimer, the term of this patent is extended or adjusted under 35 U.S.C. 154(b) by 405 days.

(21) Appl. No.: 13/171,890

(22) Filed: Jun. 29, 2011

(65) Prior Publication Data
US 2012/0004485 A1    Jan. 5, 2012

Related U.S. Application Data

(60) Provisional application No. 61/360,696, filed on Jul. 1, 2010.

(51) Int. Cl.
*B01J 29/70* (2006.01)
*C01B 39/48* (2006.01)
*C10G 50/00* (2006.01)

(52) U.S. Cl.
CPC ............... *B01J 29/70* (2013.01); *C01B 39/48* (2013.01); *C10G 50/00* (2013.01)
USPC ............. 423/707; 423/718; 502/60; 208/135

(58) Field of Classification Search
USPC ................... 423/705, 707, 708, 718; 502/60; 208/135
See application file for complete search history.

(56) References Cited

U.S. PATENT DOCUMENTS

| | | |
|---|---|---|
| 3,907,711 A | 9/1975 | Riley et al. |
| 4,472,366 A | 9/1984 | Takahashi et al. |
| 4,533,649 A | 8/1985 | Ball et al. |
| 4,899,007 A | 2/1990 | Chu et al. |
| 4,921,946 A | 5/1990 | Kocal et al. |
| 5,081,323 A | 1/1992 | Innes et al. |
| 5,389,357 A | 2/1995 | Sato et al. |
| 6,388,157 B1 | 5/2002 | Jan et al. |
| 6,613,302 B1 | 9/2003 | Moscoso et al. |
| 6,776,975 B2 | 8/2004 | Wilson et al. |
| 7,268,267 B2 | 9/2007 | Jan et al. |
| 7,578,993 B2 | 8/2009 | Lewis et al. |
| 2005/0095195 A1* | 5/2005 | Lewis et al. .......... 423/705 |
| 2012/0004483 A1 | 1/2012 | Jan et al. |

OTHER PUBLICATIONS

Xu et al., Synthesis of Small Size Crystalline Offretite in TEAOH-TMABr-AI2O3-SiO2-H2O System, Journal of Fuel Chemistry and Technology, vol. 33, No. 3, Jun. 2005, pp. 351-354, language: Chinese, abstract: English.
Van Der Puil et al., Great Promise for the Petrochemical World, ABB Review, No. 2, 2000, pp. 57-62.
Jan et al.; Synthesis Characterization and Applictions of the New Zeolit UZM-5, Studies in Surface Science and Catalysis, vol. 154 B, 2004 Elsevier B.V., pp. 1332-1340.
U.S. Appl. No. 13/330,014 filed Dec. 19, 2011, Jan et al.

\* cited by examiner

*Primary Examiner* — David M Brunsman
(74) *Attorney, Agent, or Firm* — Mark R. Willis

(57) ABSTRACT

A method for preparing a family of zeolites, examples of which have been designated UZM-5, UZM-5P and UZM-6, and are represented by the empirical formula

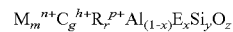

$$M_m^{n+}C_g^{h+}R_r^{p+}Al_{(1-x)}E_xSi_yO_z$$

The method includes forming a Charge Density Mismatch (CDM) reaction mixture comprising reactive sources of Al, Si, optionally a framework element, E, and at least one organic nitrogen containing cation template, C, in the hydroxide form. After the CDM mixture is mixed while aging, an organic cation crystallization template, R, and at least one alkali metal or alkaline earth metal, M, is added. The combined final reaction mixture is reacted with mixing to produce the zeolite, which may be used in various hydrocarbon conversion processes.

18 Claims, No Drawings

UZM-5, UZM-5P, AND UZM-6 CRYSTALLINE ALUMINOSILICATE ZEOLITES AND METHODS FOR PREPARING THE SAME

CROSS-REFERENCE TO RELATED APPLICATION

This application claims the benefit of U.S. Provisional Application No. 61,360,696 which was filed on Jul. 1, 2010.

FIELD OF THE INVENTION

This invention relates to a method for preparing a family of related crystalline aluminosilicate zeolites, examples of which have been designated UZM-5, UZM-5P and UZM-6. The invention also relates to zeolites of this family which have lower micropore volumes. The zeolites can catalyze various hydrocarbon processes.

BACKGROUND OF THE INVENTION

Zeolites are crystalline aluminosilicate compositions which are microporous and which have a three-dimensional oxide framework formed from corner sharing $AlO_2$ and $SiO_2$ tetrahedra. Numerous zeolites, both naturally occurring and synthetically prepared are used in various industrial processes. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure.

The number of synthetic zeolites is well over a hundred as evidenced by the *Atlas of Zeolite Structure Types* published by the International Zeolite Association (IZA). As is well known, zeolites are distinguished from each other on the basis of their composition, crystal structure and adsorption properties. One method commonly used in the art to distinguish zeolites is x-ray diffraction.

U.S. Pat. No. 6,613,302 discloses UZM-5, UZM-5P and UZM-6 as examples of a new family of crystalline aluminosilicate zeolites. Zeolites of this family are represented by the empirical formula:

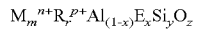
$$M_m^{n+}R_r^{p+}Al_{(1-x)}E_xSi_yO_z$$

where M is an alkali or alkaline earth metal such as lithium and strontium, R is a nitrogen containing organic cation such as tetramethyl ammonium and E is a framework element such as gallium. They are also characterized by unique x-ray diffraction patterns and have catalytic properties for carrying out various hydrocarbon conversion processes.

U.S. Pat. No. 6,388,157 discloses a process for alkylation of aromatic compounds using a new family of related crystalline aluminosilicate zeolites represented by the empirical formula:

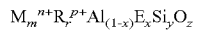
$$M_m^{n+}R_r^{p+}Al_{(1-x)}E_xSi_yO_z$$

where M is an alkali or alkaline earth metal such as lithium and strontium, R is a nitrogen containing organic cation such as tetramethyl-ammonium and E is a framework element such as gallium.

U.S. Pat. No. 7,578,993 discloses a process for preparing crystalline aluminosilicate compositions involving preparing a charge density mismatch reaction mixture comprising sources of aluminum, silicon, optionally an E metal and at least one charge density mismatch (CDM) template. The CDM template is an organic nitrogen containing template, in the hydroxide form, e.g. tetraethylammonium hydroxide and is characterized in that it is incapable of inducing crystallization. To this mixture there is added a solution comprising a second templating agent termed a crystallization template (CT). The CT can be an organic template different from the CDM template, an alkali metal, an alkaline earth metal and mixtures thereof.

SUMMARY OF THE INVENTION

Applicants have found that modification of the Charge Density Mismatch method may be used to produce members of the family of zeolites, which includes UZM-5, UZM-5P and UZM-6. It has also been discovered that the new preparation method may be used to produce zeolites having unexpectedly lower micropore volumes than previously reported for the family of zeolites.

In an embodiment, the invention is a zeolite having a composition in the as synthesized form on an anhydrous basis in terms of mole ratios of the elements given by empirical formula (1):

$$M_m^{n+}C_g^{h+}R_r^{p+}Al_{(1-x)}E_xSi_yO_z \qquad (1)$$

where M is at least one exchangeable cation selected from the group consisting of alkali and alkaline earth metals, "m" is the mole ratio of M to (Al+E) and varies from more than 0 to about 1.2, C is at least one organic nitrogen containing cation, having C/N>4 and characterized in that it is a charge density mismatch template, selected from the group consisting of quaternary ammonium ions, diquaternary ammonium ions, and quaternized alkanolammonium ions, "g" is the mole ratio of C to (Al+E) and varies from more than 0 to about 5, R is at least one crystallization-inducing organic cation which differs from C and is selected from the group consisting of quaternary ammonium ions, diquaternary ammonium ions, protonated amines, protonated diamines, protonated alkanolamines and quaternized alkanolammonium ions, "r" is the mole ratio of R to (Al+E) and has a value from more than 0 to about 3, where g+r>0.2, "n" is the weighted average valence of M and has a value of about 1 to about 2, "h" is the weighted average valence of C and has a value of about 1 to about 2, "p" is the weighted average valence of R and has a value of about 1 to about 2, E is an element selected from the group consisting of gallium, iron, boron, indium, chromium, titanium, zirconium, and mixtures thereof, "x" is the mole fraction of E and has a value from 0 to about 0.5, "y" is the mole ratio of Si to (Al+E) and varies from about 5 to about 12; "z" is the mole ratio of O to (Al+E) and has a value determined by the equation (2):

$$z=(m \cdot n+g \cdot h+r \cdot p+3+4 \cdot y)/2 \qquad (2)$$

the zeolite having (i) at least two x-ray diffraction peaks, one at a d-spacing of 3.9±0.12 Å and one at a d-spacing 8.6±0.20 Å; (ii) a tetragonal unit cell; and (iii) a micropore volume ranging from about 0.05 cc/g to less than 0.18 cc/g.

In another embodiment, the invention is a process for preparing a zeolite having a composition in the as synthesized form on an anhydrous basis in terms of mole ratios of the elements given by empirical formula (1); the zeolite having (i) at least two X-ray diffraction peaks, one at a d-spacing of 3.9±0.12 Å and one at a d-spacing 8.6±0.20 Å; and (ii) a tetragonal unit cell; the process comprising:
(a) forming a Charge Density Mismatch reaction mixture containing reactive sources of Al, Si, optionally E, and at least one C organic cation in the hydroxide form;
(b) mixing the Charge Density Mismatch reaction mixture at a temperature ranging from about 50° C. to about 100° C.

for a time ranging from about 1 hour to about 5 days to provide an aged Charge Density Mismatch mixture;

(c) adding to the aged Charge Density Mismatch mixture a crystallization inducing templating agent R organic cation and a source of M to provide a final reaction mixture having a composition expressed in terms of mole ratios of the oxides of equation (3):

$$aM_{2/n}O:bC_{2/h}O:cR_{2/p}O:(1-d)Al_2O_3:dE_2O_3:eSiO_2:fH_2O \quad (3)$$

where "a" has a value from more than 0 to about 2, "b" has a value of from more than 0 to about 25, "c" has a value from more than 0 to about 5, where c+b>0.2, "d" has a value from 0 to about 0.5, "e" has a value of about 5 to about 30 and "f" has a value of about 10 to about 5000;

(d) mixing the final reaction mixture at a temperature of about 90° C. to about 150° C. to produce the zeolite.

Yet another embodiment of the invention is a hydrocarbon conversion process using a zeolite having a composition in the as synthesized form on an anhydrous basis in terms of mole ratios of the elements given by empirical formula (1); the zeolite having (i) at least two x-ray diffraction peaks, one at a d-spacing of 3.9±0.12 Å and one at a d-spacing 8.6±0.20 Å; (ii) a tetragonal unit cell; and (iii) a micropore volume ranging from about 0.05 cc/g to less than 0.18 cc/g. More specifically, the hydrocarbon conversion process may be the alkylation of benzene with an olefin or the isomerization of xylenes.

DETAILED DESCRIPTION OF THE INVENTION

The instant invention is related to a process for preparing crystalline aluminosilicate zeolites which are characterized by a three-dimensional framework structure of at least $SiO_2$ and $AlO_2$ tetrahedral units. The zeolites are further characterized by having: (i) at least two x-ray diffraction peaks, one at a d-spacing of 3.9±0.12 Å and one at a d-spacing 8.6±0.20 Å; and (ii) a tetragonal unit cell. Exemplary zeolites produced by the method are UZM-5, UZM-5P, and UZM-6. In another aspect, the invention is a zeolite as above further characterized by having (iii) a micropore volume ranging from about 0.05 cc/g to less than 0.18 cc/g. In another aspect, the invention is related to hydrocarbon conversion processes using the zeolites.

Applicants have found that the Charge Density Mismatch (CDM) method disclosed in U.S. Pat. No. 7,578,993 may be modified and used to prepare the family of zeolites disclosed in U.S. Pat. No. 6,613,302 to produce zeolites as described in U.S. Pat. No. 6,613,302 but having a micropore volumes of less than 0.18 cc/g. The entirety of each of U.S. Pat. No. 7,578,993 and U.S. Pat. No. 6,613,302 is hereby incorporated by reference.

The zeolites of the present invention have an empirical composition on an as synthesized and anhydrous basis expressed by empirical formula (1):

$$M_m^{n+}C_g^{h+}R_r^{p+}Al_{(1-x)}E_xSi_yO_z \quad (1)$$

In the above equation, M represents at least one exchangeable cation and is selected from the group consisting of alkali and alkaline earth metals. Specific examples of the M cations include but are not limited to lithium, sodium, potassium, rubidium, cesium, calcium, strontium, barium, magnesium, and mixtures thereof. C is at least one organic cation, hereinafter referred to as the Charge Density Mismatch template, and is characterized in that it cannot crystallize the aluminosilicate composition from the reaction mixture without supplemental sources of crystallization inducing R ions. C is selected from the group of organic cations consisting of quaternary ammonium ions, diquaternary ammonium ions, and quaternized alkanolammonium ions. Preferred C organic cations have at least an atomic ratio of C/N>4 and preferably C/N>5, non-limiting examples include diethyldimethylammonium, tetraethylammonium, tetrapropylammonium, methyltriethylammonium, tetrabutylammonium, ethyltrimethylammonium, choline, hexamethonium, hexyltrimethylammonium, trimethylbutylammonium and trimethylcetylammonium ions. R is also at least one organic cation (different from C), and is distinguished from C in that it can induce crystallization of the aluminosilicate composition from the reaction mixture, is a higher charge density cation than C, is more likely to be incorporated into the zeolite than C, and is added in a much smaller portion to the reaction mixture than is C. R is an organic cation which is selected from the group consisting of quaternary ammonium ions, diquaternary ammonium ions, protonated amines, protonated diamines, protonated alkanolamines and quaternized alkanolammonium ions. Preferred organic cations are quaternary and diquaternary ammonium ions. Non-limiting examples of quaternary ammonium ions are tetramethyl-, ethyltrimethyl-, methyltriethyl, diethyldimethyl-, trimethylbutyl-, and trimethylpropyl-ammonium ions. Non-limiting examples of diquaternary ammonium ions are hexamethonium, pentamethonium, octamethonium, decamethonium, dimethylene bis (trimethylammonium), trimethylene bis(trimethylammonium), methylene bis(trimethylammonium) and tetramethylene bis(trimethylammonium). The value of "n" which is the weighted average valence of M varies from about 1 to about 2. The value of "h" which is the weighted average valence of C varies from about 1 to about 2. The value of "p" which is the weighted average valence of R varies from about 1 to about 2. The ratio of M to (Al+E) is represented by "m", which varies from more than 0 to about 1.2, "g" is the ratio of C to (Al+E) and varies from more than 0 to about 5, while "r" is the ratio of R to (Al+E) and varies from more than 0 to about 3, where g+r>0.2. The ratio of silicon to (Al+E) is represented by "y" which varies about 5 to about 12. E is an optional element, which when present, is tetrahedrally coordinated, is present in the framework, and is at least one element selected from the group consisting of gallium, iron, indium, chromium, titanium, zirconium, and boron. The mole fraction of E is represented by "x" and has a value from 0 to about 0.5, while "z" is the mole ratio of O to (Al+E) and is given by the equation (2):

$$z=(m \cdot n+g \cdot h+r \cdot p+3+4 \cdot y)/2 \quad (2)$$

Where M is only one metal, the weighted average valence is the valence of that metal, i.e. +1 or +2. However, when more than one M metal is present, the total amount of $$M_m^{n+}=M_{m1}^{(n1)+}+M_{m2}^{(n2)+}+M_{m3}^{(n3)+}+\ldots$$

and the weighted average valence "n" is given by the equation:

$$n=(m_1 \cdot n_1+m_2 \cdot n_2+m_3 \cdot n_3+\ldots)/(m_1+m_2+m_3+\ldots)$$

Similarly, when two or more C or R cations are present, the total amount of C and R are given by the equations:

$$R_r^{p+}=R_{r1}^{(p1)+}+R_{r2}^{(p2)+}+R_{r3}^{(p3)+}+\ldots$$

$$C_g^{h+}=C_{g1}^{(h1)+}+C_{g2}^{(h2)+}+C_{g3}^{(h3)+}+\ldots$$

and the weighted average valences "p" and "h" are given by the equation $$p=(r_1 \cdot p_1+r_2 \cdot p_2+r_3 \cdot p_3+\ldots)/(r_1+r_2+r_3+\ldots)$$

$$h=(g_1 \cdot h_1+g_2 \cdot h_2+g_3 \cdot h_3+\ldots)/(g_1+g_2+g_3+\ldots)$$

The sources of aluminum include but are not limited to precipitated aluminas, aluminum hydroxide, aluminum metal, aluminum salts and alumina sols. In an embodiment the aluminum source is aluminum hydroxide. Non-limiting sources of silica include but are not limited to fumed silicas, colloidal silica, and precipitated silicas. In an embodiment the silica source is colloidal silica. In another embodiment, the aluminum source is aluminum hydroxide and the silica source is colloidal silica. Sources of the E elements include but are not limited to alkali borates, boric acid, precipitated gallium oxyhydroxide, gallium sulfate, gallium nitrate, iron hydroxide, ferric sulfate, ferric chloride, chromium chloride, chromium nitrate, indium chloride, indium nitrate, titanium alkoxide, titanium chloride, zirconium alkoxide, and zirconyl chloride hydrate. As stated, the C source is required to be the hydroxide form of the organic cation. Specific examples include without limitation tetrapropylammonium hydroxide, tetraethylammonium hydroxide, methyltriethylammonium hydroxide, diethyldimethylammonium hydroxide, hexamethonium dihydroxide and ethyltrimethylammonium hydroxide. The resulting Charge Density Mismatch (CDM) reaction mixture should not be capable of crystallizing a crystalline aluminosilicate composition at the reaction temperatures at which the aluminosilicate synthesis is carried out, usually in the range of about 90° C. to about 150° C.

The CDM reaction mixture which comprises reactive sources of the desired components can be described in terms of molar ratios of the oxides by the formula:

$$bC_{2/h}O : 1\text{-}dAl_2O_3 : dE_2O_3 : eSiO_2 : fH_2O$$

"b" varies from more than 0 to about 25, "d" varies from 0 to about 0.5, "e" varies from about 5 to about 30, and "f" varies from about 10 to 5000. The CDM reaction mixture is aged with mixing at a temperature of about 50° C. to about 100° C. for a time of about 1 hour to about 5 days to provide an aged Charge Density Mismatch mixture. The CDM reaction mixture is mixed, stirred, or otherwise agitated (e.g. shaken, circulated) during this aging step. In an embodiment, the temperature during this mixing or aging step ranges from about 85° C. to about 100° C. In another embodiment, the aging time ranges from about 8 hours to about 4 days, and the aging time may range from about 12 hr to about 3 days.

To the aged CDM mixture there is admixed a crystallization inducing templating agent, R organic cation, and a source of M to provide a final reaction mixture. R and M may be premixed and added together or they may be added separately to the aged CDM mixture. This R organic cation is termed a crystallization template (CT), because it is the species that induces crystallization in the previously uncrystallizable CDM reaction mixture. The sources of R can be without limitation the halides, e.g. chlorides, carbonates, acetates or hydroxides with the hydroxides preferred. Sources of M include without limitation the halides, hydroxides, acetates, etc. In an embodiment, the source of M is selected from the group of salts consisting of halide salts, nitrate salts, sulfate salts, hydroxide salts, acetates salts, and combinations thereof.

The composition of the final reaction mixture can be expressed in terms of mole ratios of the oxides of equation (3):

$$aM_{2/n}O : bC_{2/h}O : cR_{2/p}O : (1\text{-}d)Al_2O_3 : dE_2O_3 : eSiO_2 : fH_2O \quad (3)$$

The level of (CT), R organic cation, added to the aged CDM mixture is given by "c", which represents the ratio of R to (Al+E) and varies from more than 0 to about 5, while "b" has a value from more than 0 to about 25, where c+b>0.2; "d" has a value from 0 to about 0.5, "e" has a value of about 5 to about 30 and "f" has a value of about 10 to about 5000. M, the alkali or alkaline earth metals are added to the aged CDM mixture at a level given by "a", which represents the mole ratio of M to (Al+E) and varies from more than 0 to about 2. Preferred values for "a" and "c" vary from about 0.1 to about 1 and most preferably from 0.1 to about 0.5, especially at Si/Al ratios less than 10. The higher values in the range for "a" and "c" are encountered at Si/Al ratios greater than 10 as Al concentrations become lower.

The resultant final reaction mixture is now reacted with mixing, stirring, or otherwise being agitated at a temperature of about 90° C. to about 150° C. and preferably at about 115° C. to about 135° C. for a time sufficient to produce the crystallized zeolite. Usually the reaction time is from about 12 hr to about 28 days and may range from about 2 days to about 14 days. In an embodiment, the reaction time ranges from more than 3 days to about 7 days. The reaction is usually carried out in a sealed vessel under autogenous pressure. After crystallization is complete, the solid product is isolated from the heterogeneous mixture by means such as filtration or centrifugation, and then washed with deionized water and dried in air at temperatures from ambient up to about 100° C.

As synthesized, the zeolites will contain some of the exchangeable or charge balancing cations in its pores. These exchangeable cations can be exchanged for other cations, or in the case of organic cations, they can be removed by heating under controlled conditions. All of these methods are well known in the art.

Specific examples of zeolites which can be prepared using methods of the instant invention include without limitation UZM-5, UZM-5P, and UZM-6 which can be identified by their X-ray diffraction patterns having at least the d-spacing and relative intensities set forth in Tables A, B, and C, respectively.

TABLE A

| UZM-5 | | |
|---|---|---|
| 2-θ | d(Å) | I/I$_o$ % |
| 6.31-5.89 | 14.00-15.00 | w-m |
| 7.96-7.58 | 11.10-11.65 | m-s |
| 10.40-10.01 | 8.50-8.83 | w-m |
| 12.11-11.59 | 7.30-7.63 | m |
| 16.10-15.53 | 5.50-5.70 | m-vs |
| 19.28-18.55 | 4.60-4.78 | w-m |
| 22.26-21.60 | 3.99-4.11 | m |
| 23.20-22.43 | 3.83-3.96 | w-s |
| 24.16-23.33 | 3.68-3.81 | vs |
| 30.48-29.55 | 2.93-3.02 | w-m |
| 31.94-30.92 | 2.80-2.89 | w-m |
| 44.83-43.47 | 2.02-2.08 | w |

TABLE B

| UZM-5P | | |
|---|---|---|
| 2-θ | d(Å) | I/I$_o$ % |
| 6.31-5.19 | 14.00-17.00 | w-vs |
| 7.96-7.56 | 11.10-11.70 | w-m |
| 10.52-10.04 | 8.40-8.80 | m-s |
| 16.56-15.67 | 5.35-5.65 | w-m |
| 19.49-18.87 | 4.55-4.70 | w-m |
| 23.52-22.09 | 3.78-4.02 | w-vs |
| 24.03-23.39 | 3.70-3.80 | w-vs |
| 30.81-29.76 | 2.90-3.00 | w-m |
| 31.94-30.81 | 2.80-2.90 | w-m |
| 45.30-43.04 | 2.00-2.10 | w-m |

TABLE C

UZM-6

| 2-θ | d(Å) | I/I$_o$ % |
|---|---|---|
| 6.31-5.89 | 14.00-15.00 | w-m |
| 7.96-7.58 | 11.10-11.65 | m-s |
| 10.40-10.01 | 8.50-8.83 | w-m |
| 12.11-11.59 | 7.30-7.63 | m |
| 16.10-15.53 | 5.50-5.70 | m-vs |
| 19.28-18.55 | 4.60-4.78 | w-m |
| 22.26-21.60 | 3.99-4.11 | m |
| 23.20-22.43 | 3.92-4.00 | m-vs |
| 24.16-23.33 | 3.83-3.96 | w-s |
| 30.48-29.55 | 3.68-3.81 | s-vs |
| 31.94-30.92 | 2.80-2.89 | m |
| 44.83-43.47 | 2.02-2.08 | w |

Zeolites according to the invention may be further characterized by having a micropore volume (MPV) ranging from about 0.05 cc/g to less than 0.18 cc/g. In an embodiment the micropore volume ranges from about 0.10 cc/g to less than 0.18 cc/g. In another embodiment the micropore volume ranges from about 0.11 cc/g to about 0.17 cc/g. In another embodiment, the zeolite has a micropore volume ranging from about 0.12 cc/g to about 0.16 cc/g and the micropore volume may range from about 0.13 cc/g to about 0.15 cc/g.

The zeolites of this invention are capable of separating mixtures of molecular species based on the molecular size (kinetic diameter) or on the degree of polarity of the molecular species. When the separation of molecular species is based on molecular size, separation is accomplished by the smaller molecular species entering the intracrystalline void space while excluding larger species. The kinetic diameters of various molecules such as oxygen, nitrogen, carbon dioxide, carbon monoxide are provided in D. W. Breck, *Zeolite Molecular Sieves*, John Wiley and Sons (1974) p. 636.

The crystalline microporous compositions of the present invention either as synthesized or after calcination can be used as catalysts or catalyst supports in hydrocarbon conversion processes. Hydrocarbon conversion processes are well known in the art and include cracking, hydrocracking, alkylation of both aromatics and isoparaffins, isomerization, polymerization, reforming, dewaxing, hydrogenation, dehydrogenation, transalkylation, dealkylation, hydration, dehydration, hydrotreating, hydrodenitrogenation, hydrodesulfurization, methanation and syngas shift process. Specific reaction conditions and the types of feeds which can be used in these processes are set forth in U.S. Pat. Nos. 4,310,440 and 4,440,871 which are incorporated by reference. Preferred hydrocarbon conversion processes are alkylation of aromatics and isomerization of xylenes.

Other reactions may be catalyzed by these crystalline microporous compositions, including base-catalyzed side chain alkylation of alkylaromatics, aldol-condensations, olefin double bond isomerization and isomerization of acetylenes, alcohol dehydrogenation, and olefin dimerization, oligomerization and conversion of alcohol to olefins. Suitably ion exchanged forms of these materials can catalyze the reduction of $NO_x$ to $N_2$ in automotive and industrial exhaust streams. Some of the reaction conditions and types of feeds that can be used in these processes are set forth in U.S. Pat. No. 5,015,796 and in H. Pines, THE CHEMISTRY OF CATALYTIC HYDROCARBON CONVERSIONS, Academic Press (1981) pp. 123-154 and references contained therein, which are incorporated by reference.

In order to more fully illustrate the invention, the following examples are set forth. It is to be understood that the examples are only by way of illustration and are not intended as an undue limitation on the broad scope of the invention as set forth in the appended claims.

The X-ray diffraction patterns (XRD) presented in the following examples were obtained using standard X-ray powder diffraction techniques. The radiation source was a high-intensity X-ray tube operated at 45 kV and 35 ma. The diffraction pattern from the copper K-alpha radiation was obtained by appropriate computer based techniques. Flat compressed powder samples were continuously scanned at 2° (2θ) per minute from 2° to 70° (2θ). Interplanar spacings (d) in Angstrom units were obtained from the position of the diffraction peaks expressed as 2θ where θ is the Bragg angle as observed from digitized data. Intensities were determined from the integrated area of diffraction peaks after subtracting background, "Io" being the intensity of the strongest line or peak, and "I" being the intensity of each of the other peaks.

As will be understood by those skilled in the art, the determination of the parameter 2θ is subject to both human and mechanical error, which in combination can impose an uncertainty of about ±0.4 on each reported value of 2θ and up to ±0.5 on reported values for nanocrystalline materials. This uncertainty is, of course, also manifested in the reported values of the d-spacings, which are calculated from the θ values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m and w which represent very strong, strong, medium, and weak, respectively. In terms of 100×I/I$_o$, the above designations are defined as w=0-15; m=15-60; s=60-80 and vs=80-100. In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The micropore volumes and surface areas reported in the following Examples were determined using ASTM method D4365 "Determining Micropore Volume & Zeolite Area of a Catalyst" using a Micromeritics ASAP2420 instrument or a substantially equivalent instrument. In a typical sample preparation for surface area measurement, the zeolite is first ammonium exchanged at 75° C. to lower the sodium to less than 1,000 ppm-wt $Na_2O$ on a volatile free basis. The ammonium exchanged powder is then calcined first at 350° C. and then 525° C. in flowing nitrogen, followed by air calcination at 525° C. for 5 hours, before cooling down to 100° C.

In order to more fully illustrate the invention, the following examples are set forth. It is to be understood that the examples are only by way of illustration and are not intended as an undue limitation on the broad scope of the invention as set forth in the appended claims.

EXAMPLES

Example 1

An aluminosilicate reaction mixture was prepared in the following manner. Aluminum hydroxide (26.97 wt-% Al), 23.2 g, was added to 360.2 g TEAOH (35%) with vigorous stirring. To this mixture, 289.8 g colloidal silica, (Ludox AS-40, 40% $SiO2$) was added. The reaction mixture was homogenized for 1 hr. with a high-speed mechanical stirrer, and then aged in a 2-L stirred reactor overnight at 95° C. After the aging step, a solution of 21.9 g TMAOH (25%) and 4.8 g of NaOH dissolved in 700.2 g distilled water was added to the aged mixture while applying vigorous mixing. The reactor was closed and placed in a heating mantle set at 125° C., where the reaction mixture were digested for 96 hours with continuous stirring at 150 RPM. The solid product was recovered by centrifugation, washed, and dried at 100° C.

The composition of the isolated product consisted of the mole ratios Si/Al=5.24. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 1. A portion of the sample was calcined by ramping to 525° C. at 1° C./min in N2, holding at 525° C. in N2 for 1 hr followed by a 5 hr. dwell in air, also at 525° C. The BET surface area was found to be 198 m2/g, and the micropore volume was 0.07 cc/g.

TABLE 1

| 2-θ | d(Å) | I/I$_o$ % |
|---|---|---|
| 6.07 | 14.52 | m-s |
| 7.53 | 11.71 | m |
| 10.17 | 8.68 | s |
| 11.60 | 7.62 | w |
| 15.74 | 5.62 | m |
| 18.62 | 4.76 | m |
| 20.36 | 4.35 | m |
| 21.92 | 4.05 | m |
| 22.79 | 3.89 | vs |
| 23.53 | 3.77 | s-vs |
| 26.24 | 3.39 | w |
| 26.74 | 3.33 | w |
| 27.05 | 3.29 | w |
| 30.11 | 2.96 | m |
| 30.32 | 2.94 | m |
| 30.68 | 2.91 | m |
| 31.22 | 2.86 | m |
| 32.99 | 2.71 | w |
| 43.91 | 2.05 | w |
| 52.07 | 1.75 | w |
| 53.56 | 1.70 | w |

Example 2

An aluminosilicate reaction mixture was prepared in the following manner. Aluminum hydroxide (26.97 wt-% Al), 300.3 g, was added to 3894 g TEAOH (35%) with vigorous stirring. To this mixture, 3894 g colloidal silica, (Ludox AS-40, 40% SiO2) was added. The reaction mixture was homogenized for 1 hr. with a high-speed mechanical stirrer, and then aged in a 5 gallon stirred reactor overnight at 95° C. After the aging step, a solution of 340 g TMAOH (25%) and 62.5 g of NaOH dissolved in 9647 g distilled water was added to the aged mixture while applying vigorous mixing. The reactor was closed and placed in a heating mantle set at 125° C., where the reaction mixture were digested for 111 hours with continuous stirring at 150 RPM. The solid product was recovered by centrifugation, washed, and dried at 100° C.

The composition of the isolated product consisted of the mole ratios Si/Al=5.76. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 2. A portion of the sample was calcined by ramping to 525° C. at 1° C./min in N2, holding at 540° C. in N2 for 1 hr followed by a 5 hr. dwell in air, also at 525° C. The BET surface area was found to be 305 m2/g, and the micropore volume was 0.11 cc/g.

TABLE 2

| 2-θ | d(Å) | I/I$_o$ % |
|---|---|---|
| 5.97 | 14.77 | s |
| 7.7 | 11.47 | m |
| 10.10 | 8.75 | s |
| 11.7 | 7.55 | m |
| 15.70 | 5.63 | m |
| 18.7 | 4.74 | m |
| 20.3 | 4.37 | m |
| 21.84 | 4.06 | m |
| 22.75 | 3.90 | s-vs |
| 23.58 | 3.76 | vs |
| 26.13 | 3.40 | m |
| 29.95 | 2.98 | m |
| 31.23 | 2.86 | m |
| 32.98 | 2.71 | m |
| 44.08 | 2.05 | w |
| 52.27 | 1.74 | w |

Example 3

An aluminosilicate reaction mixture was prepared in the following manner. Aluminum hydroxide (26.97 wt-% Al), 23.6 g, was added to 360.2 g TEAOH (35%) with vigorous stirring. To this mixture, 295.4 g colloidal silica, (Ludox AS-40, 40% SiO2) was added. The reaction mixture was homogenized for 1 hr. with a high-speed mechanical stirrer, and then aged in a 2-L stirred reactor overnight at 95° C. After the aging step, a solution of 21.9 g TMAOH (25%) and 4.8 g of NaOH dissolved in 700.2 g distilled water was added to the aged mixture while applying vigorous mixing. The reactor was closed and placed in a heating mantle set at 125° C., where the reaction mixture were digested for 135 hours with continuous stirring at 150 RPM. The solid product was recovered by centrifugation, washed, and dried at 100° C.

The composition of the isolated product consisted of the mole ratios Si/Al=5.66. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 3. A portion of the sample was calcined by ramping to 525° C. at 1° C./min in N2, holding at 540° C. in N2 for 1 hr followed by a 5 hr. dwell in air, also at 525° C. The BET surface area was found to be 282 m2/g, and the micropore volume was 0.11 cc/g.

TABLE 3

| 2-θ | d(Å) | I/I$_o$ % |
|---|---|---|
| 6.02 | 14.67 | s |
| 7.66 | 11.53 | m |
| 10.17 | 8.68 | s |
| 11.74 | 7.53 | w |
| 15.76 | 5.61 | m |
| 19.13 | 4.63 | w |
| 21.78 | 4.07 | m |
| 22.83 | 3.89 | vs |
| 23.56 | 3.77 | vs |
| 26.14 | 3.40 | m |
| 27.51 | 3.23 | w |
| 29.82 | 2.99 | m |
| 31.22 | 2.86 | m |
| 33.04 | 2.70 | m |
| 34.48 | 2.59 | w |
| 44.03 | 2.05 | w |

TABLE 3-continued

| 2-θ | d(Å) | I/I$_o$% |
|---|---|---|
| 52.32 | 1.74 | w |
| 54.21 | 1.69 | w |

Example 4

An aluminosilicate reaction mixture was prepared in the following manner. Aluminum hydroxide (26.97 wt-% Al), 24.46 g, was added to 313.67 g TEAOH (35%) with vigorous stirring. To this mixture, 298.75 g colloidal silica, (Ludox AS-40, 40% SiO2) was added. The reaction mixture was homogenized for 1 hr with a high-speed mechanical stirrer, and then aged in a 2-L stirred reactor overnight at 95° C. After the aging step, a solution of 23.05 g TMAOH (25%) and 5.04 g of NaOH dissolved in 735.03 g distilled water was added to the aged mixture while applying vigorous mixing. The reactor was closed and placed in a heating mantle set at 125° C., where the reaction mixture were digested for 135 hours with continuous stirring at 150 RPM. The solid product was recovered by centrifugation, washed, and dried at 100° C. Next this material was acid treated with 1000 ml of a 5% H2SO4 solution. The initial pH of this slurry was 4, further adjustment with NH4OH solution the pH of this slurry was 7.5. This slurry was stirred at room temperature for 1 hr. the solid was recovered by filtration, washed and dry at 100 C.

The composition of the isolated product consisted of the mole ratios Si/Al=6.35. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 4. A portion of the sample was calcined by ramping to 525° C. at 1° C./min in N2, holding at 525° C. in N2 for 1 hr followed by a 5 hr. dwell in air, also at 525° C. The BET surface area was found to be 348 m2/g, and the micropore volume was 0.13 cc/g.

TABLE 4

| 2-θ | d(Å) | I/I$_o$% |
|---|---|---|
| 5.81 | 15.17 | m |
| 7.54 | 11.71 | m |
| 10.18 | 8.68 | s |
| 11.78 | 7.50 | w |
| 15.64 | 5.66 | m |
| 16.48 | 5.37 | m |
| 16.93 | 5.23 | m |
| 18.67 | 4.74 | w |
| 20.42 | 4.34 | s |
| 21.88 | 4.05 | m |
| 22.83 | 3.89 | vs |
| 23.58 | 3.76 | s |
| 26.23 | 3.39 | w |
| 27.37 | 3.25 | w |
| 28.37 | 3.14 | w |
| 29.22 | 3.05 | m |
| 29.99 | 2.97 | m |
| 30.84 | 2.89 | w |
| 31.31 | 2.85 | m |
| 31.50 | 2.83 | m |
| 33.09 | 2.70 | m |
| 33.69 | 2.65 | m |
| 34.13 | 2.62 | w |
| 41.55 | 2.17 | w |
| 44.02 | 2.05 | w |
| 52.56 | 1.73 | w |

Example 5

An aluminosilicate reaction mixture was prepared in the following manner. Aluminum hydroxide (26.97 wt-% Al), 24.46 g, was added to 313.67 g TEAOH (35%) with vigorous stirring. To this mixture, 298.75 g colloidal silica, (Ludox AS-40, 40% SiO2) was added. The reaction mixture was homogenized for 1 hr with a high-speed mechanical stirrer, and then aged in a 2-L stirred reactor overnight at 95° C. After the aging step, a solution of 23.05 g TMAOH (25%) and 5.04 g of NaOH dissolved in 735.03 g distilled water was added to the aged mixture while applying vigorous mixing. The reactor was closed and placed in a heating mantle set at 125° C., where the reaction mixture were digested for 135 hours with continuous stirring at 150 RPM. The solid product was recovered by centrifugation, washed, and dried at 100° C.

The composition of the isolated product consisted of the mole ratios Si/Al=5.39. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 5. A portion of the sample was calcined by ramping to 525° C. at 2° C./min in N2, holding at 525° C. in N2 for 1 hr followed by a 5 hr. dwell in air, also at 525° C. The BET surface area was found to be 416 m2/g, and the micropore volume was 0.14 cc/g.

TABLE 5

| 2-θ | d(Å) | I/I$_o$% |
|---|---|---|
| 6.02 | 14.67 | m |
| 7.62 | 11.58 | m |
| 10.13 | 8.71 | s |
| 11.68 | 7.57 | m |
| 15.70 | 5.63 | m |
| 16.47 | 5.37 | m |
| 18.73 | 4.73 | m |
| 20.34 | 4.36 | w |
| 21.76 | 4.08 | m |
| 22.79 | 3.89 | s |
| 23.58 | 3.76 | vs |
| 26.22 | 3.39 | m |
| 27.48 | 3.24 | w |
| 29.94 | 2.98 | m |
| 30.76 | 2.90 | m |
| 31.28 | 2.85 | m |
| 33 | 2.71 | m |
| 34.86 | 2.57 | w |
| 43.92 | 2.05 | w |
| 52.29 | 1.74 | w |

Example 6

An aluminosilicate reaction mixture was prepared in the following manner. Aluminum hydroxide (26.97 wt-% Al), 300.3 g, was added to 3894 g TEAOH (35%) with vigorous stirring. To this mixture, 3894 g colloidal silica, (Ludox AS-40, 40% SiO2) was added. The reaction mixture was homogenized for 1 hr with a high-speed mechanical stirrer, and then aged in a 5 gallon stirred reactor overnight at 95° C. After the aging step, a solution of 340 g TMAOH (25%) and 62.5 g of NaOH dissolved in 9647 g distilled water was added to the aged mixture while applying vigorous mixing. The reactor was closed and placed in a heating mantle set at 125° C., where the reaction mixture were digested for 96 hours with continuous stirring at 150 RPM. The solid product was recovered by centrifugation, washed, and dried at 100° C.

The composition of the isolated product consisted of the mole ratios Si/Al=5.35. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 6. A portion of the sample was calcined by ramping to 525° C. at 2° C./min in N2, holding at 525° C. in N2 for 1 hr followed by a 5 hr dwell in air, also at 525° C. The micropore volume was 0.15 cc/g.

TABLE 6

| 2-θ | d(Å) | I/I$_o$ % |
|---|---|---|
| 6.15 | 14.33 | m |
| 7.64 | 11.56 | m |
| 10.13 | 8.71 | s |
| 11.72 | 7.54 | m |
| 15.80 | 5.60 | m |
| 16.37 | 5.40 | m |
| 18.75 | 4.72 | m |
| 20.34 | 4.36 | w |
| 21.88 | 4.05 | s |
| 22.75 | 3.90 | s |
| 23.62 | 3.76 | vs |
| 24.90 | 3.57 | w |
| 26.21 | 3.39 | m |
| 26.96 | 3.30 | w |
| 27.51 | 3.23 | w |
| 30.02 | 2.97 | m |
| 30.64 | 2.91 | m |
| 31.3 | 2.85 | m |
| 33.12 | 2.70 | m |
| 34.49 | 2.59 | w |
| 44.13 | 2.05 | w |
| 52.51 | 1.74 | w |
| 54.28 | 1.68 | w |

Example 7

An aluminosilicate reaction mixture was prepared in the following manner. Aluminum hydroxide (26.97 wt-% Al), 23.2 g, was added to 360.2 g TEAOH (35%) with vigorous stirring. To this mixture, 289.8 g colloidal silica, (Ludox AS-40, 40% SiO2) was added. The reaction mixture was homogenized for 1 hr with a high-speed mechanical stirrer, and then aged in a 2-L stirred reactor overnight at 95° C. After the aging step, a solution of 21.09 g TMAOH (25%) and 4.9 g of NaOH dissolved in 700.2 g distilled water was added to the aged mixture while applying vigorous mixing. The reactor was closed and placed in a heating mantle set at 125° C., where the reaction mixture were digested for 96 hours with continuous stirring at 150 RPM. The solid product was recovered by centrifugation, washed, and dried at 100° C.

The composition of the isolated product consisted of the mole ratios Si/Al=5.39. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 7. A portion of the sample was calcined by ramping to 525° C. at 2° C./min in N2, holding at 525° C. in N2 for 1 hr followed by a 5 hr. dwell in air, also at 525° C. The BET surface area was found to be 467 m2/g, and the micropore volume was 0.16 cc/g.

TABLE 7

| 2-θ | d(Å) | I/I$_o$ % |
|---|---|---|
| 6.09 | 14.47 | m |
| 7.64 | 11.56 | m |
| 10.21 | 8.64 | s |
| 11.76 | 7.51 | m |
| 15.75 | 5.61 | m |
| 18.99 | 4.66 | m |
| 21.92 | 4.05 | s |
| 22.86 | 3.88 | vs |
| 23.72 | 3.74 | vs |
| 26.25 | 3.39 | m |
| 27.02 | 3.29 | m |
| 27.25 | 3.26 | m |
| 30.01 | 2.97 | m |
| 31.31 | 2.85 | m |
| 33.14 | 2.70 | m |
| 34.73 | 2.58 | w |
| 44.084 | 2.05 | w |
| 52.64 | 1.73 | w |
| 54.11 | 1.69 | w |

Example 8

An aluminosilicate reaction mixture was prepared in the following manner. Aluminum hydroxide (26.97 wt-% Al), 24.46 g, was added to 313.67 g TEAOH (35%) with vigorous stirring. To this mixture, 298.75 g colloidal silica, (Ludox AS-40, 40% SiO2) was added. The reaction mixture was homogenized for 1 hr with a high-speed mechanical stirrer, and then aged in a 2-L stirred reactor overnight at 95° C. After the aging step, a solution of 23.05 g TMAOH (25%) and 5.04 g of NaOH dissolved in 735.03 g distilled water was added to the aged mixture while applying vigorous mixing. The reactor was closed and placed in a heating mantle set at 125° C., where the reaction mixture were digested for 135 hours with continuous stirring at 150 RPM. The solid product was recovered by centrifugation, washed, and dried at 100° C.

The composition of the isolated product consisted of the mole ratios Si/Al=5.63. Scanning Electron Microscopy (SEM) showed the crystallites to consist of clustered platelets approximately 300-500 nm across. Powder X-ray diffraction of the product showed the pattern to be consistent with that for UZM-5P. Characteristic lines in the X-ray diffraction pattern are shown in Table 8. A portion of the sample was calcined by ramping to 525° C. at 2° C./min in N2, holding at 525° C. in N2 for 1 hr followed by a 5 hr. dwell in air, also at 525° C. The BET surface area was found to be 412 m2/g, and the micropore volume was 0.17 cc/g.

TABLE 8

| 2-θ | d(Å) | I/I$_o$ % |
|---|---|---|
| 5.66 | 15.59 | m |
| 7.66 | 11.53 | m |
| 10.12 | 8.73 | s |
| 11.74 | 7.53 | m |
| 15.74 | 5.62 | m |
| 18.9 | 4.69 | m |
| 20.32 | 4.36 | w |
| 21.76 | 4.08 | s |
| 22.70 | 3.91 | s |
| 23.5 | 3.78 | vs |
| 26.23 | 3.39 | m |
| 26.89 | 3.31 | w |
| 27.43 | 3.24 | w |
| 29.85 | 2.98 | m |
| 31.3 | 2.85 | m |
| 33.02 | 2.71 | m |
| 37.83 | 2.37 | w |

TABLE 8-continued

| 2-θ | d(Å) | I/I_o % |
|---|---|---|
| 43.88 | 2.06 | w |
| 52.37 | 1.74 | w |
| 54.31 | 1.68 | w |

Example 9

An aluminosilicate reaction mixture was prepared in the following manner. Aluminum hydroxide (26.97 wt-% Al), 23.6 g, was added to 305.7 g TEAOH (35%) with vigorous stirring. To this mixture, 295 g colloidal silica, (Ludox AS-40, 40% SiO2) was added. The reaction mixture was homogenized for 1 hr with a high-speed mechanical stirrer, and then aged in a 2-L stirred reactor overnight at 95° C. After the aging step, a solution of 26.7 g TMAOH (25%) and 4.9 g of NaOH dissolved in 744.1 g distilled water was added to the aged mixture while applying vigorous mixing. The reactor was closed and placed in a heating mantle set at 125° C., where the reaction mixture were digested for 96 hours with continuous stirring at 150 RPM. The solid product was recovered by centrifugation, washed, and dried at 100° C.

The composition of the isolated product consisted of the mole ratios Si/Al=5.84. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 9. A portion of the sample was calcined by ramping to 525° C. at 1° C./min in N2, holding at 525° C. in N2 for 1 hr followed by a 5 hr dwell in air, also at 525° C. The BET surface area was found to be 453 m2/g, and the micropore volume was 0.17 cc/g.

TABLE 9

| 2-θ | d(Å) | I/I_o % |
|---|---|---|
| 5.9 | 14.96 | m |
| 7.58 | 11.65 | m |
| 10.06 | 8.78 | s |
| 11.58 | 7.63 | m |
| 15.63 | 5.66 | m |
| 16.30 | 5.43 | m |
| 18.73 | 4.73 | m |
| 20.28 | 4.37 | w |
| 21.84 | 4.06 | m |
| 22.68 | 3.91 | s |
| 23.48 | 3.78 | vs |
| 26.15 | 3.40 | m |
| 27.00 | 3.29 | w |
| 27.44 | 3.24 | w |
| 29.88 | 2.98 | m |
| 30.72 | 2.90 | m |
| 31.22 | 2.86 | m |
| 32.92 | 2.71 | m |
| 34.31 | 2.61 | w |
| 36.44 | 2.46 | w |
| 43.92 | 2.05 | w |
| 52.40 | 1.74 | w |
| 53.91 | 1.69 | w |

Example 10

An aluminosilicate reaction mixture was prepared in the following manner. Aluminum hydroxide (26.97 wt-% Al), 37.5 g, was added to 481.2 g TEAOH (35%) with vigorous stirring. To this mixture, 464.3 g colloidal silica, (Ludox AS-40, 40% SiO2) was added. The reaction mixture was homogenized for 1 hr with a high-speed mechanical stirrer, and then aged in a 2-L stirred reactor overnight at 95° C. After the aging step, a solution of 35 g TMAOH (25%) and 7.7 g of NaOH dissolved in 374.1 g distilled water was added to the aged mixture while applying vigorous mixing. The reactor was closed and placed in a heating mantle set at 125° C., where the reaction mixture were digested for 72 hours with continuous stirring at 100 RPM. The solid product was recovered by centrifugation, washed, and dried at 100° C.

The composition of the isolated product consisted of the mole ratios Si/Al=6.13. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 10. A portion of the sample was calcined by ramping to 525° C. at 1° C./min in N2, holding at 525° C. in N2 for 1 hr followed by a 5 hr dwell in air, also at 525° C. The BET surface area was found to be 597 m2/g, and the micropore volume was 0.2 cc/g.

TABLE 10

| 2-θ | d(Å) | I/I_o % |
|---|---|---|
| 6 | 14.71 | m |
| 7.72 | 11.44 | m |
| 10.13 | 8.71 | m-s |
| 11.82 | 7.48 | m |
| 15.78 | 5.61 | m |
| 16.46 | 5.38 | m |
| 18.8 | 4.71 | m |
| 20.36 | 4.35 | m |
| 21.28 | 4.17 | m |
| 21.89 | 4.05 | s |
| 22.74 | 3.90 | s |
| 23.56 | 3.77 | vs |
| 25.02 | 3.55 | w |
| 26.21 | 3.39 | m |
| 27.16 | 3.28 | m |
| 28.92 | 3.08 | w |
| 30.04 | 2.97 | m |
| 30.74 | 2.90 | w |
| 31.26 | 2.85 | m |
| 33.02 | 2.71 | m |
| 34.34 | 2.60 | w |
| 44.12 | 2.05 | w |
| 52.44 | 1.74 | w |
| 53.96 | 1.69 | w |

The invention claimed is:

1. A zeolite having a composition in the as synthesized form, on an anhydrous basis, in terms of mole ratios of the elements given by the empirical formula

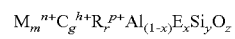

$$M_m^{n+}C_g^{h+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from more than 0 to about 1.2, C is at least one organic nitrogen containing cation, having C/N>4 and characterized in that it is a charge density mismatch template, selected from the group consisting of quaternary ammonium ions, diquaternary ammonium ions, and quaternized alkanolammonium ions, "g" is the mole ratio of C to (Al+E) and varies from more than 0 to about 5, R is at least one crystallization-inducing organic cation which differs from C and is selected from the group consisting of quaternary ammonium ions, diquaternary ammonium ions, protonated amines, protonated diamines, protonated alkanolamines and quaternized alkanolammonium ions, "r" is the mole ratio of R to (Al+E) and has a value from more than 0 to about 3, where g+r>0.2, "n" is the weighted average valence of M and has a value of about 1 to about 2, "h" is the weighted average valence of C and has a value of about 1 to about 2, "p" is the weighted average valence of R and has a value of about 1 to about 2, E is an element selected from the group consisting of gallium, iron, boron, indium, chromium, titanium, zirconium, and mixtures thereof, "x" is the mole fraction of E and has a value from 0 to about 0.5, "y" is the mole ratio of Si to (Al+E) and varies from about 5 to about 12; "z" is the mole ratio of O to (Al+E) and has a value determined by the equation $$z=(m\cdot n+g\cdot h+r\cdot p+3+4\cdot y)/2$$

the zeolite having (i) at least two x-ray diffraction peaks, one at a d-spacing of 3.9±0.12 Å and one at a d-spacing 8.6±0.20 Å; (ii) a tetragonal unit cell; and (iii) a micropore volume ranging from about 0.05 cc/g to less than 0.18 cc/g.

2. The zeolite of claim 1 wherein the zeolite has a X-ray powder diffraction pattern which contains at least the d-spacings and relative intensities of one of Tables A, B, and C.

3. The zeolite of claim 1 wherein C is selected from the group of organic nitrogen containing cations consisting of tetrapropylammonium, tetraethylammonium, diethyldimethylammonium, methyltriethylammonium, tetrabutylammonium, ethyltrimethylammonium, choline, hexamethonium, hexyltrimethylammonium, trimethylbutylammonium, trimethylcetylammonium, and mixtures thereof.

4. The zeolite of claim 1 wherein R is selected from the group of quaternary ammonium ions consisting of tetramethylammonium, ethyltrimethylammonium, diethyldimethylammonium, methyltriethylammonium, trimethylbutylammonium, trimethylpropylammonium, and mixtures thereof.

5. The zeolite of claim 1 wherein M is at least one metal selected from the group consisting of lithium, cesium, sodium, potassium, strontium, barium, calcium, and magnesium, and R is a quaternary ammonium cation.

6. The zeolite of claim 5 wherein M is sodium and the R comprises a tetramethylammonium ion.

7. The zeolite of claim 1 wherein M is a mixture of an alkali metal and an alkaline earth metal and R is a quaternary ammonium cation.

8. The zeolite of claim 1 wherein M comprises sodium, C comprises a tetraethylammonium cation, and R comprises a tetramethylammonium cation.

9. The zeolite of claim 1 further comprising E wherein "x" has a value from about 0.05 to about 0.5.

10. The zeolite of claim 9 wherein E comprises at least one of gallium, iron, boron, and titanium.

11. The zeolite of claim 1 wherein the micropore volume ranges from about 0.10 cc/g to about 0.17 cc/g.

12. A process for preparing a zeolite having a composition in the as synthesized form on an anhydrous basis in terms of mole ratios of the elements given by the empirical formula

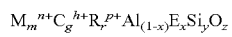

where M is at least one exchangeable cation selected from the group consisting of alkali and alkaline earth metals, "m" is the mole ratio of M to (Al+E) and varies from more than 0 to about 1.2, C is at least one organic nitrogen containing cation, having C/N>4 and characterized in that it is a charge density mismatch template, selected from the group consisting of quaternary ammonium ions, diquaternary ammonium ions, and quaternized alkanolammonium ions, "g" is the mole ratio of C to (Al+E) and varies from more than 0 to about 5, R is at least one crystallization-inducing organic cation which differs from C and is selected from the group consisting of quaternary ammonium ions, diquaternary ammonium ions, protonated amines, protonated diamines, protonated alkanolamines and quaternized alkanolammonium ions, "r" is the mole ratio of R to (Al+E) and has a value from more than 0 to about 3, where g+r>0.2, "n" is the weighted average valence of M and has a value of about 1 to about 2, "h" is the weighted average valence of C and has a value of about 1 to about 2, "p" is the weighted average valence of R and has a value of about 1 to about 2, E is an element selected from the group consisting of gallium, iron, boron, indium, chromium, titanium, zirconium, and mixtures thereof, "x" is the mole fraction of E and has a value from 0 to about 0.5, "y" is the mole ratio of Si to (Al+E) and varies from about 5 to about 12; "z" is the mole ratio of O to (Al+E) and has a value determined by the equation $$z=(m\cdot n+g\cdot h+r\cdot p+3+4\cdot y)/2$$

the zeolite having (i) at least two x-ray diffraction peaks, one at a d-spacing of 3.9±0.12 Å and one at a d-spacing 8.6±0.20 Å; (ii) a tetragonal unit cell; and (iii) a micopore volume ranging from about 0.05 cc/g to less than 0.18 cc/g; the process comprising:

(a) forming a Charge Density Mismatch reaction mixture at a temperature of about 90° C to about 150° C., the Charge Density Mismatch reaction mixture comprising reactive sources of Al, Si, optionally E, and at least one C organic cation in the hydroxide form, the source of aluminum being aluminum hydroxide;

(b) mixing the Charge Density Mismatch reaction mixture at a temperature ranging from about 50° C. to about 100° C. for a time ranging from about 1 hour to about 5 days to provide an aged Charge Density Mismatch mixture;

(c) adding to the aged Charge Density Mismatch mixture a crystallization inducing templating agent R organic cation in the hydroxide form and a source of M to provide a final reaction mixture having a composition expressed in terms of mole ratios of the oxides of

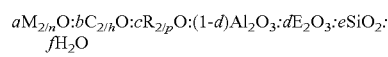

where "a" has a value from more than 0 to about 2, "b" has a value of more than 0 to about 25, c" has a value from more than 0 to about 5, where c+b>0.2, "d" has a value from 0 to about 0.5, "e" has a value of about 5 to about 30 and "f" has a value of about 10 to about 5000;

(d) mixing the final reaction mixture at a temperature of about 90° C. to about 135° C. to produce the zeolite.

13. The process of claim 12 wherein C is selected from the group of organic nitrogen containing cations consisting of tetrapropylammonium, tetraethylammonium, diethyldimethylammonium, methyltriethylammonium, tetrabutylammonium, ethyltrimethylammonium, choline, hexamethonium, hexyltrimethylammonium, trimethylbutylammonium, trimethylcetylammonium, and mixtures thereof.

14. The process of claim 12 wherein R is selected from the group of quaternary ammonium ions consisting of tetramethylammonium, ethyltrimethylammonium, diethyldimethylammonium, methyltriethylammonium, trimethylbutylammonium, trimethylpropylammonium, and mixtures thereof.

15. The process of claim 12 wherein M is at least one metal selected from the group consisting of lithium, cesium, sodium, potassium, strontium, barium, calcium, and magnesium.

16. The process of claim 12 wherein the silicon source is selected from the group consisting of fumed silica, colloidal silica and precipitated silica.

17. A hydrocarbon conversion process comprising contacting a hydrocarbon stream with a zeolite at hydrocarbon conversion conditions to give a converted product, the zeolite having a composition in the as synthesized form on an anhydrous basis in terms of mole ratios of the elements given by the empirical formula $$M_m^{n+}C_g^{h+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from more than 0 to about 1.2, C is at least one organic nitrogen containing cation, having C/N>4 and characterized in that it is a charge density mismatch template, selected from the group consisting of quaternary ammonium ions, diquaternary ammonium ions, and quaternized alkanolammonium ions, "g" is the mole ratio of C to (Al+E) and varies from more than 0 to about 5, R is at least one crystallization-inducing organic cation which differs from C and is selected from the group consisting of quaternary ammonium ions, diquaternary ammonium ions, protonated amines, protonated diamines, protonated alkanolamines and quaternized alkanolammonium ions, "r" is the mole ratio of R to (Al+E) and has a value from more than 0 to about 3, where g+r>0.2, "n" is the weighted average valence of M and has a value of about 1 to about 2, "h" is the weighted average valence of C and has a value of about 1 to about 2, "p" is the weighted average valence of R and has a value of about 1 to about 2, E is an element selected from the group consisting of gallium, iron, boron, indium, chromium, titanium, zirconium, and mixtures thereof, "x" is the mole fraction of E and has a value from 0 to about 0.5, "y" is the mole ratio of Si to (Al+E) and varies from about 5 to about 12; "z" is the mole ratio of O to (Al+E) and has a value determined by the equation $$z=(m \cdot n+g \cdot h+r \cdot p+3+4 \cdot y)/2$$

the zeolite having (i) at least two x-ray diffraction peaks, one at a d-spacing of 3.9±0.12 Å and one at a d-spacing 8.6±0.20 Å; (ii) a tetragonal unit cell; and (iii) a micropore volume ranging from about 0.05 cc/g to less than 0.18 cc/g.

18. The process of claim 17 where the hydrocarbon conversion process is selected from the group consisting of alkylation, transalkylation, isomerization, olefin dimerization, olefin oligomerization, and dewaxing.

* * * * *